US005487895A

United States Patent [19]
Dapper et al.

[11] Patent Number: 5,487,895
[45] Date of Patent: Jan. 30, 1996

[54] METHOD FOR FORMING CONTROLLED RELEASE POLYMERIC SUBSTRATE

[75] Inventors: Gregory S. Dapper, Newark; Ronald K. Yamamoto, San Francisco, both of Calif.

[73] Assignee: Vitaphore Corporation, Plainsboro, N.J.

[21] Appl. No.: 106,342

[22] Filed: Aug. 13, 1993

[51] Int. Cl.⁶ .............................. A61K 39/00; A61K 9/52
[52] U.S. Cl. ...................... 424/278.1; 424/484; 424/499; 424/184.1; 514/774; 514/776; 514/773; 530/356; 530/354; 530/409
[58] Field of Search ................................... 530/356, 354; 424/484, 499, 184.1, 278.1; 514/774, 776, 773

[56] References Cited

U.S. PATENT DOCUMENTS

| | | |
|---|---|---|
| 3,427,301 | 2/1969 | Needles et al. . |
| 3,469,003 | 9/1969 | Haver-Lockhart . |
| 4,061,787 | 12/1977 | Higgins . |
| 4,140,537 | 2/1979 | Luck et al. . |
| 4,233,360 | 11/1980 | Luck et al. . |
| 4,280,954 | 7/1981 | Yannas et al. . |
| 4,294,241 | 10/1981 | Miyata . |
| 4,404,033 | 9/1983 | Steffan et al. . |
| 4,448,718 | 5/1984 | Yannas et al. . |
| 4,500,453 | 2/1985 | Shank . |
| 4,535,010 | 8/1985 | Axen et al. . |
| 4,582,640 | 4/1986 | Smestad et al. . |
| 4,590,020 | 5/1986 | Itaba et al. . |
| 4,597,762 | 7/1986 | Walter et al. . |
| 4,703,108 | 10/1987 | Silver et al. . |
| 4,808,399 | 2/1989 | Rypacek et al. . |
| 4,824,620 | 4/1989 | Casa et al. . |
| 4,863,647 | 9/1989 | Baylor . |
| 4,882,150 | 11/1989 | Kaufman . |
| 4,892,700 | 1/1990 | Guerra et al. . |
| 4,923,699 | 5/1990 | Kaufman . |
| 4,923,700 | 5/1990 | Kaufman . |
| 4,948,540 | 8/1990 | Nigam . |
| 4,958,008 | 9/1990 | Petite et al. . |
| 4,969,912 | 11/1990 | Kelman et al. . |
| 4,970,298 | 11/1990 | Silver et al. ............................ 530/356 |
| 4,971,954 | 11/1990 | Brodsky et al. ......................... 514/21 |
| 4,981,912 | 1/1991 | Kurihara . |
| 5,024,742 | 6/1991 | Nesburn et al. . |

FOREIGN PATENT DOCUMENTS

| | | |
|---|---|---|
| 0210461 | 7/1986 | European Pat. Off. . |
| 0367590 | 11/1989 | European Pat. Off. . |
| 91918644 | 11/1993 | European Pat. Off. . |
| 8904668 | 6/1989 | WIPO . |
| 9110446 | 7/1991 | WIPO . |

OTHER PUBLICATIONS

Horakova, Z., et al. "Prolongation of Various Pharmacological Effects by Means of Collagen Substances", Thérapie, vol. 22, 1967, pp. 1455–1460 and Translation from French.

M. Chvapil, R. Kronenthal, W. van Winkle; Medical and Surgical Applications of Collagen; Int. Rev. Conn. Tissres, 6:1–61 (1973).

M. Dunn, T. Miyata, K. Stenzel, A. Rubin; Studies on Collagen Implants in the Vitreous; Surgical Forum/Ophthalmic Surgery, vol. 19, 492–494 (1968).

A. Rubin, K. Stenzel; Collagen as a Biomaterial; Technology Review, vol. 71, No. 2, 44–49 (1968).

E. Balazs, D. B. Sweeney; A. McPherson (ed.); The Injection of Hyaluronic Acid and Reconstituted Vitreous into the Vitreous Cavity; New and Controversial Aspects of Retinal Detachment, 36:371–376 (1968).

(List continued on next page.)

Primary Examiner—Kay K. A. Kim
Attorney, Agent, or Firm—Fish & Richardson

[57] ABSTRACT

A method for forming a controlled release polymeric substrate is provided by contacting a polymeric substrate with a liquid mixture containing a cross-linking agent at least partially soluble therein comprising water and an organic liquid, for a period of time and at a temperature and concentration of the agent sufficient for the agent to penetrate the substrate to form cross-linking bridges in the substrate in a decreasing concentration gradient beneath the surface.

23 Claims, 4 Drawing Sheets

OTHER PUBLICATIONS

S. Richard–Blum, G. Ville; Minireview: Collagen Crosslinking; *Int. J. Biochem.,* vol. 21, No. 11, 1185–1189 (1989).

M. Chvapil, D. Speer, W. Mora, C. Eskelson; Effect of Tanning Agent on Tissue Reaction to Tissue Implanted Collagen Sponge; *Journal of Surgical Research,* 35, 402–409 (1983).

K. Weadock, R. Olson, F. Silver; Evaluation of Collagen Crosslinking Techniques; *Biomat., Med., Dev., Art. Org.,* 11 (4), 293–318 (1983–84).

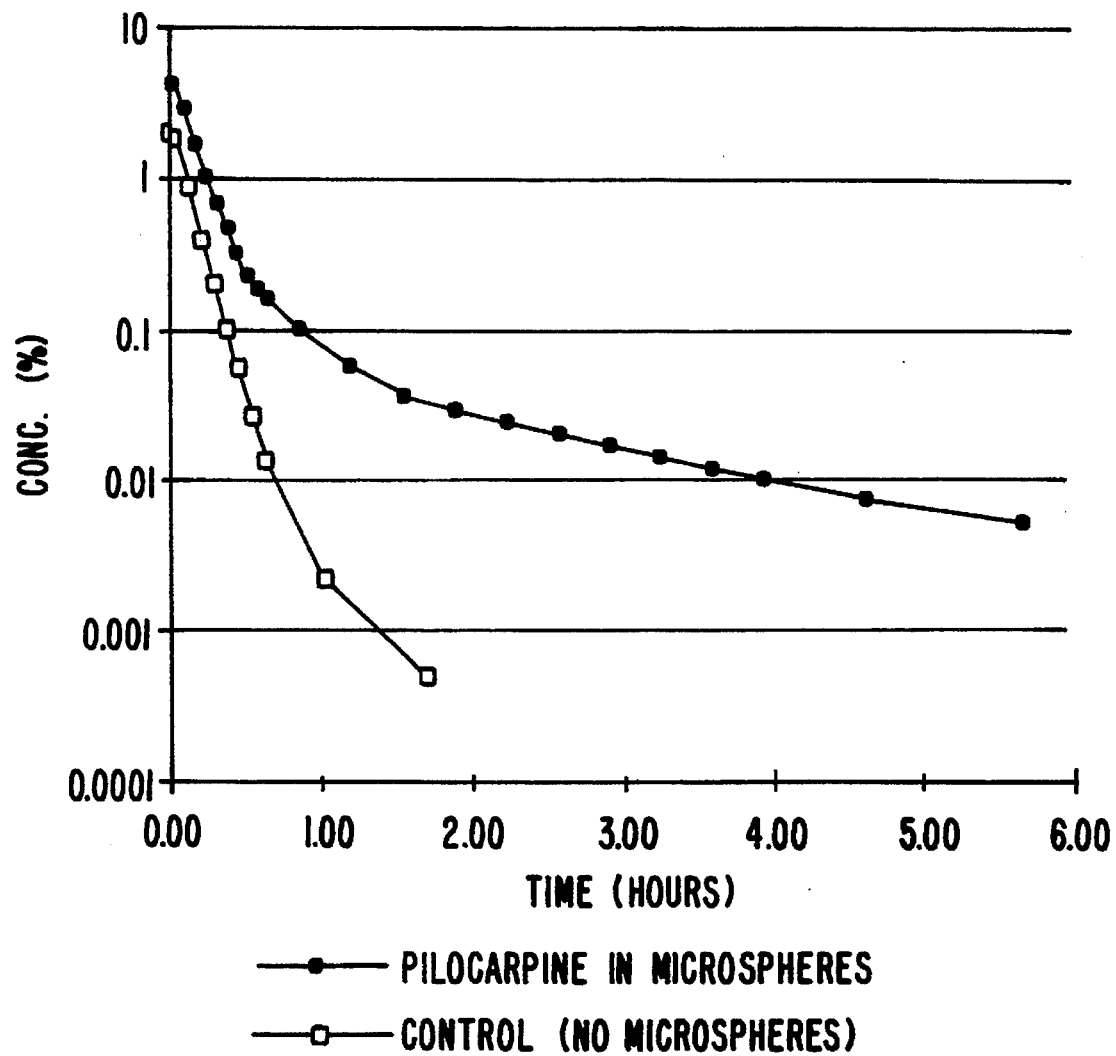

METHOD FOR FORMING CONTROLLED RELEASE POLYMERIC SUBSTRATE

FIELD OF THE INVENTION

The present invention relates to a method for forming controlled release polymeric substrates which release bioactive materials in a time-release fashion, by diffusion through the substrate and/or bioerosion of the substrate. The invention is particularly directed to the use of collagen or collagen-like substrates which are cross-linkable.

BACKGROUND OF THE INVENTION

It is desirable in a great number of biomedical fields to be able to provide controlled release of bioactive agents into body tissues or fluids. However, due to the multiplicity of the types of chemical structures of bioactive agents, the desired time-release profile for a particular bioactive agent, and the diffusion rates in available and desirable substrates and/or bioerosion of such substrates in bodily fluids, it can be difficult to determine the proper combination of substrate/ bioactive agent for a suitable time-release profile, if any. In addition, it would be desirable in some cases to have a substrate in a particular shape, such as a lens for use as an ocular insert for treatment of corneal transplant trauma.

It is thus an object of the present inventions to provide a method for making collagen and collagen-like substrates which are adapted through cross-linking for time-release profiles of bioactive agents.

It is a particular object of the present invention to provide ocular inserts whereby the outer surface of the ocular insert is protected against excessive dehydration by cross-linking while the inner surface of the insert is relatively uncrosslinked to allow for the release of the bioactive agent into the tear fluid.

These and other objects of the invention will be apparent from the following description of the invention, the appended claims and from practice of the invention.

BACKGROUND OF THE INVENTION

U.S. Pat. No. 4,535,010 to Axen, issued Aug. 13, 1985, discloses a method for coating a solid body or substrate with polymeric layers which are formed by cross-linking an organic substance. The primary object of that invention is to coat a substrate, such as plastics, for example, Plexiglas® (polymethylmethacrylate), polystyrene, polyvinyl alcohol, polyvinyl chloride and polyethylene. Porous substrates are also disclosed such as gel chromatographic media, for example, Sephadex®, crosslinked dextran and Sepheron®, crosslinked poly(hydroxyalkylmethacrylate). The substrate is first pre-impregnated with a component which is necessary for the cross-linking reaction which, when contacted with a solution, tends to diffuse from the substrate into the solution. If the solution contains a component which prevents the cross-linking reaction from occurring when the component diffuses from the substrate, the cross-linking can only take place in the boundary layer of the solution and the substrate, thereby forming a coating over the substrate. Alternatively, the substrate may be impregnated with a modulator (such as hydroxyl ions) which diffuses into the solution. At the boundary layer between solution and substrate the modulator contacts the other cross-linking components in the solution thus causing the cross-linking condition to take place at the boundary layer. The disclosure in this patent does not appear to provide a cross-linking gradient into the substrate beneath the surface nor does it appear to disclose a method for entrapping a bioactive agent within the substrate to control release therefrom.

U.S. Pat. No. 4,981,912 to Kurihara, issued Jan. 1, 1991, discloses a method for forming shaped articles of a crosslinked elastomer having a crosslinked density continuously decreasing from the surface toward the interior at a specific gradient. The articles are characterized by surface non-stickiness and low friction properties while maintaining tensile strength, elongation and compression set resistant properties as well as elastomeric properties. The purpose of this invention is apparently to modify the surface characteristics of the elastomeric substrate while maintaining or improving other bulk properties.

The elastomeric substrates which are disclosed include natural rubber, polybutadiene, styrene-butadiene copolymer, polychloroprene rubber, ethylene propylene copolymer, ethylene-propylene-diene terpolymer and various other isomeric substrates such as silicone rubber, urethane rubber, acrylic rubber, fluorosilicone rubber and the like, all of which are non-water soluble. The elastomer is first vulcanized using a cross-linking agent which partially crosslinks the elastomer at a substantially uniform cross-linking density throughout the entire body of the substrate. Sulfur and sulfite compounds, oximes, and quinones are disclosed as being useful for this purpose. The surface of the vulcanized elastomer is then treated with a second cross-linking agent to provide a second partial crosslinked density at the surface of the substrate. The second partial crosslinked density, however, decreases continuously from the surface toward the interior of the substrate. The second cross-linking agents are disclosed to be such compounds as the sulfite compounds, phosphorous containing polysulfates, oximes, quinones, peroxides and others. The velocity of cross-linking may be controlled by the use of cross-linking promoters and accelerators. Since the first and second cross-linking agents may be the same or very similar reagents, the uniform cross-linking reaction and the gradient cross-linking reaction may be controlled by selecting appropriate immersion conditions, such as concentration of the ingredients, temperature and time of immersion. The end products are disclosed as being useful as oil seals, gaskets, O-rings, cable covers and other uses for nonsticky, low friction articles. Since the elastomeric substrates disclosed in this patent are non-water soluble, and thus, not swellable in water, they are not useful in accordance with the present invention.

There have been suggestions for uses of collagen in ophthalmology but the focus has been on the problems of reabsorption and optical clarity. Balazsl, "New and Controversial Aspects of Retinal Detachment", A. McPherson, editor, page 371, Harper, New York (1968), injected hyaluronic acid and a mixture of hyaluronic acid and collagen (reconstituted vitreous) into the vitreous cavities of owl monkeys. With reconstituted vitreous, less transparency was noted, and upon injection into the eye the solution gelled and did not mix with water. In studies on 50 owl monkeys, both the hyaluronic acid and the vitreous disappeared in four to five months and were replaced by the animals' own vitreous. Dunn, et al., Surg. Forum 19, 492 (1968); and Rubin, et al., Tech. Rev. 71 (Number 2) (1969) used gels made from enzyme-treated collagen as a vitreous replacement. They found that gels could be stabilized by reducing agents such as ascorbic acid. Ultraviolet irradiation was used to crosslink the gel and increase stability. Rubin, et al. also used extruded collagen gels as implants to relieve glaucoma. However, no details of the preparation or procedures were given.

There have been some studies for the uses of collagen in a drug delivery system. It is assumed that collagen-formed complexes with various substances of varying stability dissociate slowly when administered subcutaneously, intramuscularly and intraperitoneally, therefore prolonging the pharmacological action of the drug. See Horakova, et al., Therapie 22, 1455 (1967). Hardy, U.S. Pat. No. 3,469,003, injected patients with vaccines and other drugs using reconstituted collagen as a vehicle. The effectiveness of local anesthetics such as procaine and lidocaine, analgesics (pethidine) and neuroplagique (perathiapine) was extended three to five times when compared with controls injected with the drug alone. However, this observation is possibly explained by retardation of the diffusion of the drug into the systemic circulation by the viscous collagen-drug complex.

However, it is believed that there has not been a suggestion in the art to form collagen-shaped articles having a surface which is crosslinked below such surface in a decreasing concentration gradient of cross-linking sites in order to control the release rate of a drug within the device.

Moreover, there has been no suggestion to surface crosslink microspheres of collagen for use as controlled release drug delivery vehicles.

It is thus an object of the present invention to provide a method for forming collagen-shaped articles which are crosslinked, at least on one surface thereof, to control the release of the drug absorbed into the collagen from that surface.

It is another object of the present invention to provide ophthalmic inserts of collagen which are crosslinked at one surface thereof to retard dehydration and drug release through that surface, but uncrosslinked at the opposite surface, to promote drug release.

It is yet another object of the present invention to provide collagen microspheres, which are crosslinked to a depth having a decreasing concentration gradient, which not only controls and retards diffusion of the drug from the microspheres but also controls and retards bioerosion of the microsphere.

These and other objects of the present invention will be apparent from the following description, the appended claims and from the practice of the invention.

SUMMARY OF THE INVENTION

The present invention provides a method for forming a controlled release polymeric substrate comprising the steps of contacting a water-swellable polymeric substrate or a portion thereof, with a mixture containing a cross-linking agent in a liquid carrier comprising water and an organic liquid for a period of time, at a temperature and at a concentration of the agent sufficient for the agent to penetrate the surface of the substrate and form cross-linking bridges in the substrate in a decreasing concentration gradient beneath the surface. The concentration of the organic liquid in the liquid carrier is sufficient to prevent dissolution of any significant amount of the substrate while in contact with the liquid carrier.

The crosslinked substrate is then preferably loaded with the bioactive agent by soaking in a solution of the bioactive agent. The method is particularly adaptable for preparing microspheres of crosslinked substrates which contain the bioactive agent. Upon contact of the loaded microspheres with body fluids or tissues the microspheres are gradually eroded by the action of enzymes or other active agents in the body fluids or tissues, or impregnated within the microspheres.

BRIEF DESCRIPTION OF THE DRAWINGS

In the accompanying figures:

FIG. 4 is a graph of the time release profile of pilocarpine from microspheres made according to Example 6.

DESCRIPTION OF THE PREFERRED EMBODIMENTS

Figure 1:
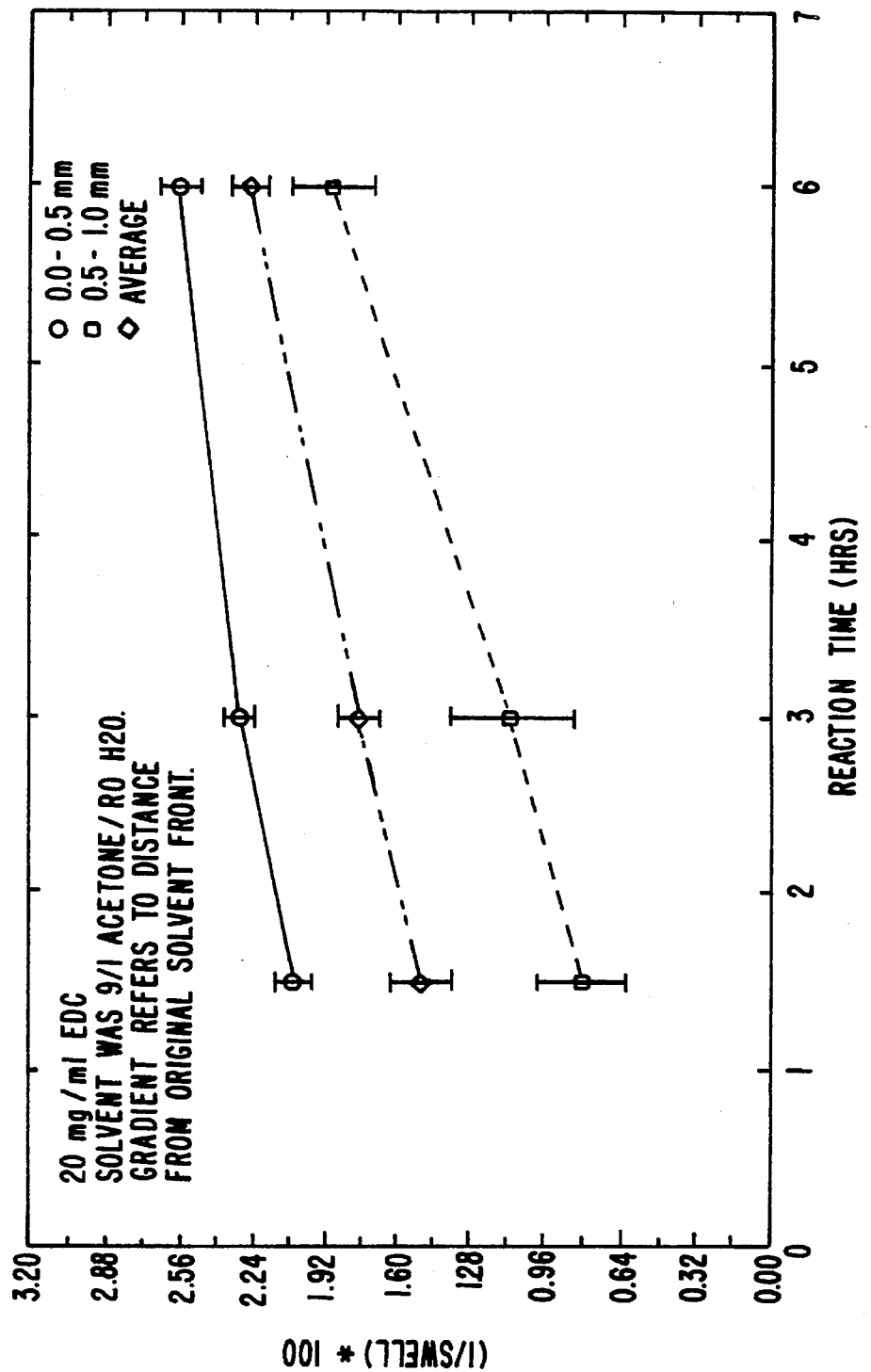
FIG. 1 is a graph of the swell gradient for crosslinked collagen gels as a function of reaction time of the gel with the cross-linking agent EDC.

According to the present invention there is provided a method for forming a controlled release polymeric substrate which is crosslinked on at least one surface thereof in a decreasing concentration gradient of crosslinks beneath the surface. The cross-linking is performed with a cross-linking agent which is contacted with the substrate in the presence of a liquid carrier comprising water and an organic liquid. The cross-linking agent should be at least partially soluble in the solvent mixture of the organic liquid and water.

The substrate which may be crosslinked according to the present invention to form controlled release articles include water-swellable proteinaceous material such as collagen, gelatin, elastin, albumin, chitosan (deacetylated chitin), and other polymeric materials which have functional moieties such as amino groups, carboxyl groups and hydroxyl groups which can serve as handles for the cross-linking reaction. Other substrates include polymeric materials having hydroxyl and carboxyl functionalities as functional handles for cross-linking such as glycocyamine glycosoamino glycans (hyaluronic acid, chondroitin sulfate, dermatin sulfate, heparin, etc.); polyacrylic acid; cellulose and cellulose derivatives; alginate polymers; and amino functional polymers, carboxyl or hydroxyl functional polymers such as hydroxyl and carboxyl functional polymers listed above combined with amino functional polymers such as chitosan or protein such as collagen. The preferred substrates are collagen in any of its natural or modified forms.

Bioactive agents include, but are not limited to antibiotics, analgesics, anti-inflammation agents, anti-glaucoma agents, vaccines, anti-neoplastic agents, etc. Representative anti-glaucoma agents are Timolol, Epinephrine, Betaxolol, Pilocarpine, and Carbonic Anhydrase Inhibitors. Representative antibiotics are Tobramycin, Gentamycin, and Ciprofloxcin. Analgesics, anti-neoplastic agents and vaccines include Cidocaine, Proparacaine, 5-FU, Methotrexate, and inactivated viruses. These bioactive agents may be used alone, or in combination, depending upon the desired therapy. The amount of bioactive agent incorporated into the substrate will depend upon the surface area and volume of the substrate, the period of contact of the substrate with the bioactive agent containing solution during loading of the substrate, and concentration of the solution. Incorporation of the desired dosage of bioactive agent into the substrate may be readily achieved by variation of one or more of these parameters. The substrate is typically loaded by soaking in a solution of the bioactive agent, preferably after the substrate has been cross-linked. In some instances, the substrate may be loaded before cross-linking, recognizing that some of the bioactive agent may be lost during the subsequent cross-linking process.

The cross-linking agent should be at least partially soluble in the water and organic solvent mixture. The preferred reagents are the water-soluble carbodiimides, in particular 1-ethyl-3-(3-diethylaminopropyl) carbodiimide (EDC) and 1-cyclohexyl-3-(2-(3'-morpholino)-ethyl) carbodiimide (CMC). Preferably, these agents are used at an initial concentration in the solvent in the range of about 0.1 to 10 mg/ml.

The solvent mixture in which the cross-linking reaction is conducted is preferably a mixture of water and an organic water-miscible solvent such as a ketone, alcohol, ester, etc. The preferred organic solvent is acetone. Representative organic solvents include alcohols such as methanol and ethanol, ketones such as acetone and methylethyl ketone, esters such as ethyl acetate, carbon disulfide and mixtures thereof.

The substrate is water-swellable so that when it is in contact with the solvent containing the cross-linking agent, the water content in the solvent will cause the substrate to swell thereby facilitating penetration of the cross-linking agent into the substrate. Generally the liquid mixture used to contact the substrate for cross-linking will comprise from 5% to 95% by volume of the organic solvent, with the remaining being water. The organic solvent preferably limits the penetration of the cross-linking agent, which is preferably water-soluble. Therefore, by increasing the organic solvent content in the mixture, the depth of the cross-linking agent penetration into the substrate can be reduced. By control of the time of contact of the substrate with the swelling solvent and the cross-linking agent, the temperature, concentration of agent and concentration of organic solvent in the mixture, the depth of penetration of the cross-linking agent into the substrate can be controlled, as well as the crosslinked density, which is continuously decreasing from the surface of the substrate to the point at which there is no cross-linking. For example, when the shape of the collagen device is a thin film, such as for an ocular bandage, which itself is only about 100 microns thick, it may be desirable to crosslink one surface (the outer surface) of the bandage and to have a gradual gradient of decreasing cross-linking density into the thickness of the film achieving a cross-linking density of zero before penetration to the opposite (inner) surface. In this manner the outer surface of the ocular bandage will have the highest density of cross-linking thereby minimizing the loss of bioactive agent and moisture through the outward facing surface, while still allowing the release of the bioactive agent through the uncrosslinked inner surface facing the retina where the bioactive agent is most needed. The uncrosslinked surface also advantageously provides a hydrated, cushioning surface against the eye.

In another embodiment the collagen may be formed into microspheres, then impregnated with the bioactive agent and an enzyme which degrades collagen, such as Collagenase or Cathepsin. The microspheres may be formed and preserved in a relatively dry state in which the enzyme is inactive. Upon exposing the microspheres to body tissues or fluids, the collagen will hydrate and swell, and the enzyme will be activated. However, since the area in which the least amount of cross-linking is present is at the interior of the microsphere, degradation will occur the fastest in the interior of the microsphere. The last portion of the microsphere to degrade will be the outer surface or shell where there is maximum cross-linking. Upon penetration of the shell by degradation, the microsphere will collapse and the remaining bioactive agent will be released.

The cross-linking agent concentration is generally in the range of 0.01 to 5 percent by weight in the aqueous:organic solvent mixture. Cross-linking accelerators may be utilized, as appropriate. The temperature of immersion is preferably in the range of about 4° C. to about 50° C. and the time of immersion is appropriately selected within the range of about 5 seconds to about 72 hours. A useful period of immersion is from 0.05 to 24 hours.

After the immersion, the article is removed from the treating solution and preferably soaked in purified water. The substrate may be treated with the bioactive agent before or after cross-linking, as appropriate. For example, if the collagen is in the shape of a microsphere the collagen will first be treated with a bioactive agent and other agent, such as an enzyme, which is to be retained within the microsphere, then the outer surface of the microsphere is crosslinked in accordance with the present invention.

The invention is illustrated by the following examples which are not intended to limit the invention in any way.

EXAMPLE 1

A collagen dispersion (2% bovine hide source) was prepared at pH 3.8, and added to 13×100 mm borosilicate test tubes in such a manner as to produce 13×10 mm cylindrical collagen gels. To each test tube was added 8ml of an appropriate cross-linking system which contained EDC in an acetone/water solvent mixture. Before the reaction was quenched, the cylindrical collagen gels were removed from the tubes and sliced into two nearly equal segments (approximately 13×5 mm). The top segment and the bottom segment were then placed into two different test tubes. Each test tube contained 8ml of acetic acid (quenching agent). After 18 hours, the swelled segments were weighted, wet and then dry. The inverse of swell was evaluated as a function of the following parameters: 1) reaction time, 2) EDC concentration, and 3) the ratio of acetone to water in the reaction solvent. The inverse of swell was evaluated because it is relevant to the actual crosslink density. The inverse of the dry volume fraction of a polymer in a solvent is proportional to the crosslink density of the polymer. By varying the extent of reaction time while holding the concentration of EDC at 20 mg/ml and the ratio of acetone to water in the reaction solvent at 9/1, matrices with measurable crosslink gradients were produced. The inverse of the swell of the matrices was plotted as a function of the extent of reaction time (FIG. 1). The inverse of the swell for the top slice, the bottom slice, and the average of both were plotted. Each data point was then averaged for 10 samples. There was a significant difference in swell from the top of it to the bottom of each piece tested after 1.5, 3.0 and 6.0 hours. Crosslink gradient can be controlled by limiting the extent of reaction through the gel. If the reaction is quenched before the cross-linking system diffuses to the entire gel, the part of the gel which has not come into contact with the cross-linking system will have a lower crosslink density than the parts in the gel which were in contact with the cross-linking system. The longer the gel remains in contact with the cross-linking system, the faster the matrix will approach a uniform crosslink density.

EXAMPLE 2

Figure 2:
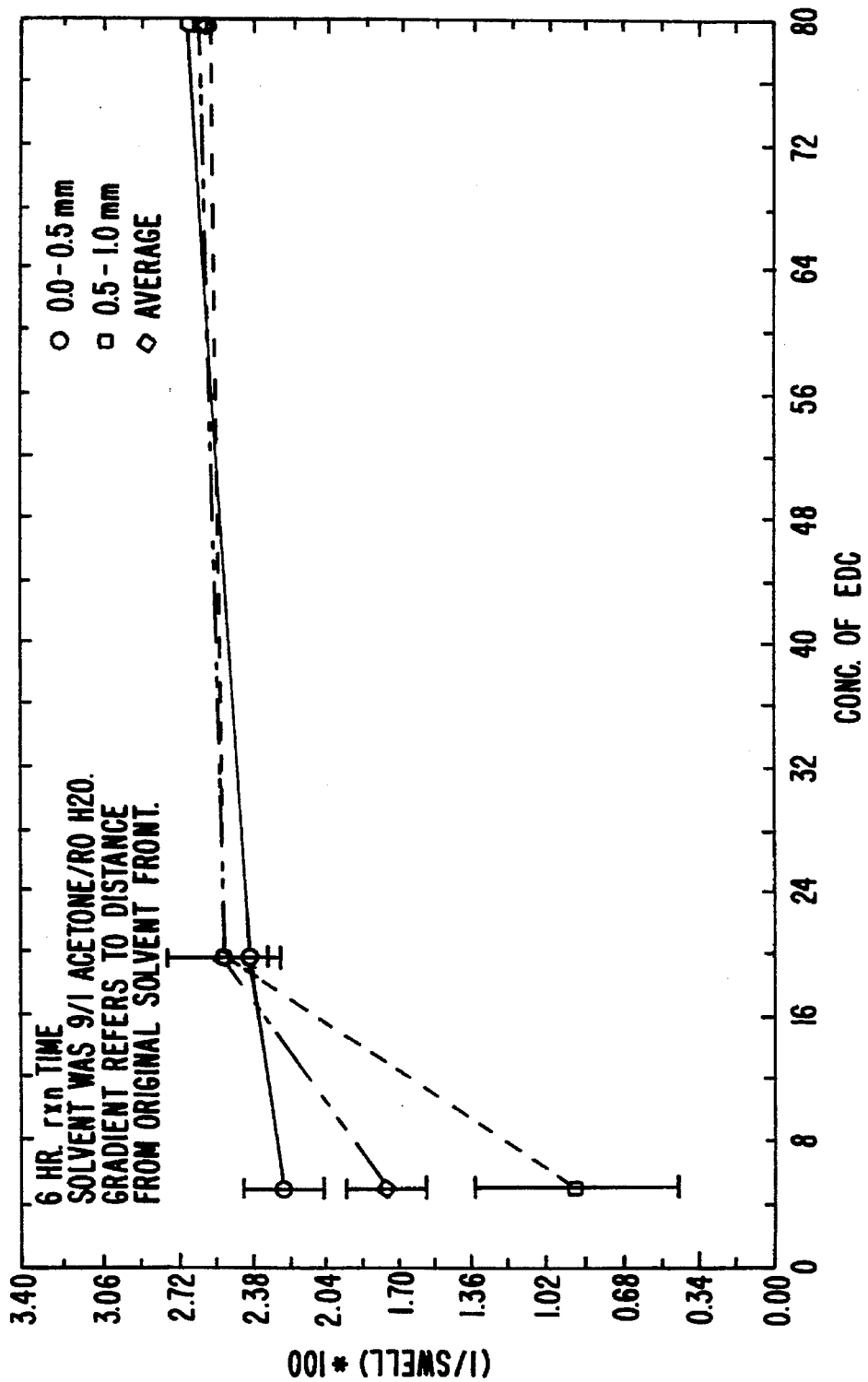
FIG. 2 is a graph of the swell gradient for crosslinked collagen gels as a function of EDC concentration.

Concentration of EDC was increased from 5 to 80 mg/ml while holding the reaction time at 6 hours and the ratio of acetone to water in the reaction solvent at 9/1, the swell gradient from top to bottom decreased. See FIG. 2. The reaction proceeded more rapidly as the concentration of EDC was increased. This shows that one may increase the crosslink density gradient for materials crosslinked at higher EDC concentrations by reducing the extent of reaction time or limiting the diffusion of the cross-linking system.

EXAMPLE 3

Figure 3:
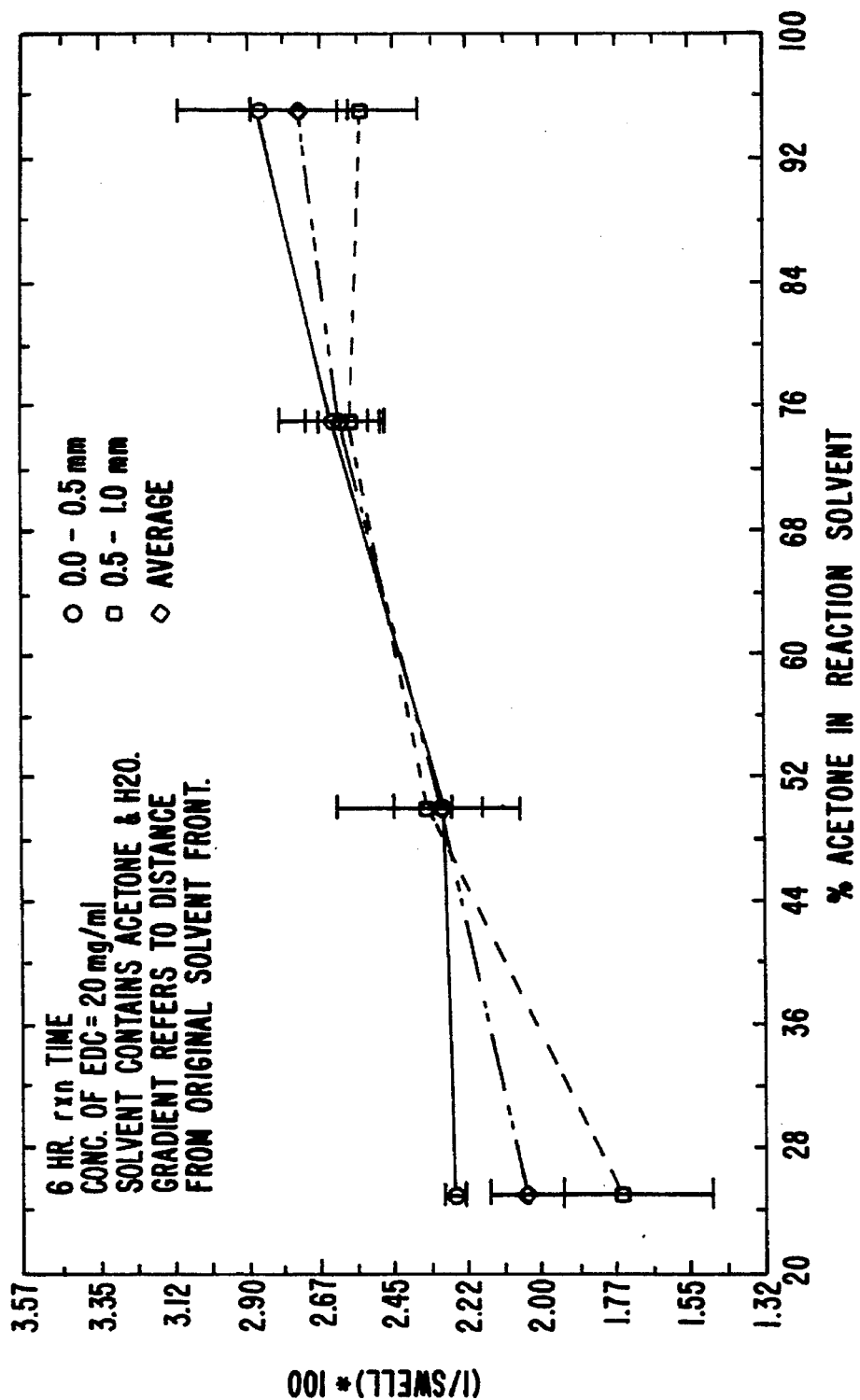
FIG. 3 is a graph of the swell gradient of crosslinked collagen gels as a function of acetone concentration in the reaction solvent.

To evaluate the effect of solvent systems, the swell was monitored and plotted as a function of the ratio of acetone to water in the reaction solvent while holding the concentration of EDC at 20 mg/ml and the extent of reaction time at 6 hours. Examination of FIG. 3 indicates that a ratio of 1/3 acetone to water in the reaction solvent creates a significant difference in the crosslink density from the top to the bottom of the collagen gels tested. As the acetone to water ratio was increased to 3/1, there was no longer any observable difference in swell from top to bottom. When the acetone to water ratio was increased to 9.5/0.5, the difference in crosslink density from top to bottom reappeared. This may be explained by the following. At higher water concentrations the hydrolysis of the activated ester and EDC impedes the desired amide bond formation needed to crosslink the matrix. Therefore as the solvent front proceeds through the gel the amount of EDC available for cross-linking is decreased (due to hydrolysis) thereby forming a crosslink density gradient. As the acetone concentration was increased to greater than 75 percent, the diffusion of the cross-linking system was slowed, which in turn may have caused the observed gradient at 95 percent acetone.

EXAMPLE 4

Preparation of Hydrogel Micro spheres

Two grams of collagen was dissolved into 100 ml of distilled water with gentle agitation. After the collagen had completely dissolved the pH of the solution was adjusted to 6.0 with a solution of sodium hydroxide or hydrochloric acid. Two grams of poly-acrylic acid (Carbopol 934 P, Goodyear) was dissolved into 100 ml of distilled water with gentle agitation. After the poly-acrylic acid had completely dissolved the pH of the solution was adjusted to 6.0 with a solution of sodium hydroxide or hydrochloric acid.

Five grams of the collagen solution was combined with 5 grams of acrylate solution and diluted with 10 ml of distilled water. To this solution, 4 grams of sorbitan monooleate was added and the resulting mixture was thoroughly mixed. Using a high shear mixer, 25 ml of toluene was slowly added and an emulsion was formed. The resulting emulsion was poured into 8 volumes of acetone with gentle mixing. A dispersion of microspheres was formed. A solution of 15 mg of ethyldimethylaminopropyl carbodiimide (EDC) in 1 ml of water and 9 ml of acetone was added to the dispersion. The mixture was allowed to react for 1 hour.

The microspheres were isolated by centrifugation. The isolated microspheres were resuspended into 30 ml of acetone and isolated by centrifugation. This procedure was repeated 2 more times. The acetone washed microspheres were suspended in 40 ml of 5 mM acetate buffer (pH=5) and then isolated by centrifugation. The procedure was repeated 2 time substituting distilled water for acetate buffer. Two ml of water were added to the isolated microsphere to yield a concentrated slurry of microspheres.

EXAMPLE 5

Drug Loading of Hydrogel Microspheres

Three hundred thirty ul of concentrated slurry, prepared as described in Example 4, was added to 670 ul of a 7.5% pilocarpine solution. The solution was gently mixed for 5 min. The resulting solution contains drug loaded microspheres. The amount of the pilocarpine incorporated into the microspheres was determined by measuring the concentration of pilocarpine in the aqueous portion of the microsphere dispersion and comparing that to the amount of pilocarpine added to the solution, the difference being the amount incorporated in to the microsphere.

EXAMPLE 6

Ocular Model In-Vitro Release of a Drug from Microspheres

A dispersion of drug loaded microspheres, prepared as described in Example 5, was placed into a 500 ul reservoir with 2 openings on opposite sides was filled with an aqueous solution of drug. The reservoir contained a 0.45 um filter between the two openings. The inlet was connected to a peristaltic pump via silicone tubing. The reservoir was perfused with physiological saline solution and the eluate was collected. The rate of perfusion was adjusted such that the rate of elimination of drug from the reservoir was comparable to the rate of elimination of a drug from the tear film of the eye. The concentration of drug in the eluate was determined by UV spectroscopy and graphed versus time, shown in FIG. 4.

EXAMPLE 7

Preparation of Hollow Spheres

A mixture of 230 ml of acetone, 20 ml of RO water, and 125 mg of ethyl-(dimethylaminopropyl)carbodiimide hydrochloride is made in a 250 ml graduated cylinder. The solution was mixed thoroughly. A two percent dispersion of hydrolyzed bovine tendon collagen (SEMEX II) at pH 3.8 was then added to the graduated cylinder dropwise with a 7.5 ml polyethylene disposable transfer pipet. Approximately 30 drops of collagen dispersion were added to the reaction mixture. After intervals of five, ten, and twenty minutes, ten of the collagen drops were removed, and placed in a vial containing RO water. After soaking in RO for twenty minutes, each vial containing the crosslinked collagen material collected at each time interval was photographed. A crosslinked droplet of collagen was then removed from each vial, and dissected into three slices, so that the center slice formed a doughnut shape. The cross-section of the center slices for each time interval was magnified and photographed.

The photographs showed that the spheres were hollow. In addition, the time progression results show that the thickness of the shell can be controlled by varying the crosslinking time. As the crosslink density of a collagen matrix increases the percent hydration of the collagen matrix decreases. Thus, the collagen matrices become less dense than water as the crosslink density is increased.

What is claimed is:

1. A method of forming a controlled release polymer substrate comprising the steps of:

a) providing a water-swellable polymeric substrate;

b) contacting said substrate, or a portion thereof, with a liquid mixture containing a cross-linking agent which is at least partially soluble in said liquid mixture comprising water and an organic liquid, for a period of time and at a temperature and concentration of said agent sufficient for said agent to penetrate a surface of said substrate in contact with said mixture, to form cross-linking bridges in said substrate in a decreasing concentration gradient beneath said surface;

c) contacting said substrate with a bioactive agent which is absorbed into said substrate.

2. A method according to claim 1 wherein said substrate comprises a film and one surface of said film is contacted with said mixture in step (b).

3. A method according to claim 1 wherein said substrate comprises droplets of a dispersion of a polymeric material, whereby upon said contacting in said step (c), said substrate is formed into hollow spheres.

4. A method according to claim 1 wherein said period of time, temperature and concentration are selected to form a crosslinked skin on said substrate.

5. A method for releasing a bioactive agent through a first surface of a polymer substrate in a controlled manner into body tissue or fluid comprising the step of contacting said tissue or fluid with said surface of said substrate loaded with said bioactive agent; said substrate characterized by a decreasing concentration gradient of cross-linking bridges beneath a second surface thereof wherein said bioactive agent is selectively released from said substrate primarily through said first surface of said substrate wherein said second surface is proximal to the end of said gradient having a low concentration of said cross-linking bridges.

6. A method for time-releasing a bioactive agent into body fluid or tissue comprising the step of contacting said fluid or tissue with particles comprising a water-swellable polymeric material, said microspheres impregnated with said bioactive material, wherein said particles are characterized by a decreasing concentration gradient of cross-linking bridges from the outer surface toward the interior such that upon contact of said particles with said body fluid or tissue, said particles release said bioactive agent.

7. A method according to claim 6 wherein such particles further are impregnated with an active agent which acts upon said polymeric material to erode said particles from the interior thereof, whereby upon contact of said particles with said body fluid or tissue said active agent commences erosion of said particles whereby the rate of said erosion is higher at areas of low density of cross-linking bridges in the interior of said particles and the last portion of said particles to erode is at the surface of said particles where the density of cross-linking bridges is greatest.

8. A method according to claim 6 or 7 wherein said particles comprise hollow spheres.

9. A method according to claim 1 wherein said substrate is selected from the group consisting of collagen, gelatins, elastins, albumins and chitosans.

10. A method according to claim 9 wherein said substrate is selected from the group consisting of natural and modified collagens.

11. A method according to claim 1 wherein said cross-linking agent is selected from the group consisting of 1-ethyl-3-(3-diethylaminopropyl carbodiimide and 1-cyclohexyl-3-(2-(3'-morpholino)ethyl) carbodiimide.

12. A method according to claim 1 wherein said organic liquid is selected from the group consisting of ketones, alcohols, esters and mixtures thereof.

13. A method according to claim 12 wherein said organic liquid is selected from the group consisting of methanol, ethanol, acetone, methylethyl ketone, ethyl acetate, and mixtures thereof.

14. A method according to claim 1 wherein said organic liquid comprises a water-immiscible solvent.

15. A method according to claim 1 wherein said liquid mixture comprises from 5% to 95% organic solvent and 95% to 5% water by volume.

16. A method according to claim 11 wherein said concentration of said crosslinking agent initially in said liquid mixture is in the range of 0.1 to 10 mg/ml.

17. A method according to claim 1 wherein period of time of contact of said substrate with said liquid mixture is in the range of 0.05 to 24 hours.

18. A method according to claim 1 wherein said temperature is in the range of 4° C. to 50° C.

19. A method according to claim 1 wherein said bioactive agent is selected from the group consisting of antibiotics, analgesics, anti-inflammatory agents, anti-glaucoma agents, vaccines, and anti-neoplastic agents.

20. A method according to claim 1 wherein said step (c) precedes said step (b).

21. A cross-linked controlled-release polymer substrate containing a bioactive agent prepared according to any one of claims 1 through 4 or 9 through 20.

22. A method according claim 5 wherein said substrate comprises collagen crosslinked with 1-ethyl-3-(3-diethylaminopropyl) carbodiimide.

23. A method according to claim 6 or 7 wherein said polymeric material comprises collagen crosslinked with 1-ethyl-3-(3-diethylaminopropyl) carbodiimide.

* * * * *

UNITED STATES PATENT AND TRADEMARK OFFICE
CERTIFICATE OF CORRECTION

PATENT NO.   : 5,487,895
DATED        : January 30, 1996
INVENTOR(S)  : Gregory S. Dapper and Ronald K. Yamamoto It is certified that error appears in the above-identified patent and that said Letters Patent is hereby corrected as shown below:

Title Page:  Attorney, Agent, or Firm —change "Fish & Richardson" to --Fish & Richardson P.C.--.

Column 7, line 65:  change "time" to --times--.

Column 8, line 14:  change "in to" to --into--.

Column 10, line 44:  after the word "according" insert the word --to--.

Signed and Sealed this

Twenty-sixth Day of November 1996

Attest:

BRUCE LEHMAN

*Attesting Officer*  *Commissioner of Patents and Trademarks*